United States Patent
Vinteler

(10) Patent No.: US 10,251,963 B2
(45) Date of Patent: Apr. 9, 2019

(54) METHOD FOR DRYING A MEDICAL DEVICE

(71) Applicant: PLASMABIOTICS, Evry (FR)

(72) Inventor: Daniel Vinteler, Issy les Moulineaux (FR)

(73) Assignee: PLASMABIOTICS, Evry (FR)

( * ) Notice: Subject to any disclaimer, the term of this patent is extended or adjusted under 35 U.S.C. 154(b) by 1 day.

(21) Appl. No.: 15/514,008

(22) PCT Filed: Sep. 25, 2015

(86) PCT No.: PCT/FR2015/052557
§ 371 (c)(1),
(2) Date: Mar. 24, 2017

(87) PCT Pub. No.: WO2016/046503
PCT Pub. Date: Mar. 31, 2016

(65) Prior Publication Data
US 2017/0274108 A1    Sep. 28, 2017

(30) Foreign Application Priority Data

Sep. 25, 2014   (FR) ...................................... 14 59071

(51) Int. Cl.
| | | |
|---|---|---|
| *A61L 2/14* | (2006.01) | |
| *A61B 1/12* | (2006.01) | |
| *A61B 90/70* | (2016.01) | |

(52) U.S. Cl.
CPC ................ *A61L 2/14* (2013.01); *A61B 1/121* (2013.01); *A61B 2090/701* (2016.02); *A61L 2202/24* (2013.01)

(58) Field of Classification Search
CPC ..... A61L 2/14; A61L 2/16; A61L 2/18; A61L 2/183; A61L 2/186; A61L 2/24;
(Continued)

(56) References Cited

U.S. PATENT DOCUMENTS 5,882,589 A     3/1999  Mariotti
6,641,781 B2 *  11/2003 Walta ..................... A61B 1/123
                                                          134/26
(Continued)

FOREIGN PATENT DOCUMENTS

FR     2 705 896 A1    12/1994
FR     2 790 962 A1     9/2000
(Continued)

OTHER PUBLICATIONS

International Search Report, dated Dec. 2, 2015, from corresponding PCT application.

*Primary Examiner* — Timothy C Cleveland
(74) *Attorney, Agent, or Firm* — Young & Thompson

(57) ABSTRACT

Disclosed is a method for drying endoscope channels, including the following steps: a) connecting the endoscope, particularly via a specific connection, to a plasma drying unit; b) injecting a neutral gas into the endoscope channels for a duration of 10 to 60 seconds, the flow rate of the gas being low, the gas being injected at a temperature of 10° C. to 30° C. such as to eliminate residual water; then c) drying the endoscope channels, for a duration of 30 to 150 seconds, by injecting a gas at a high flow rate, the gas being injected at a temperature of 30° C. to 60° C.

16 Claims, 2 Drawing Sheets

(58) Field of Classification Search
CPC ....... A61L 2/26; A61L 2202/24; A61B 1/121; A61B 1/123; A61B 1/125; A61B 2090/701
See application file for complete search history.

(56) References Cited

U.S. PATENT DOCUMENTS

2006/0283483 A1   12/2006  Pieroni et al.
2009/0229632 A1    9/2009  Labib et al.

FOREIGN PATENT DOCUMENTS

| FR | 2 843 028 A1 | 2/2004 |
|----|----|----|
| WO | 02/070025 A1 | 9/2002 |
| WO | 2005/000366 A2 | 1/2005 |

* cited by examiner

METHOD FOR DRYING A MEDICAL DEVICE

FIELD OF THE INVENTION

The present invention relates to a quick method for drying an endoscope with one or more channels. The present invention also relates to a method for storing an endoscope with one or more channels.

BACKGROUND OF THE INVENTION

Endoscopy is a medical imaging technique that is widely used at the present time, in particular because of its ease of implementation, its precision and its low invasive cost. Endoscopes are thus used either to establish a diagnosis (diagnostic endoscopy) or treat an illness or injury (operative endoscopy). The handling and cleaning thereof are however very specific: cleaning and disinfection are necessary.

Conventionally, the endoscope is cleaned immediately after the examination, with a suitable non-abrasive detergent, and then rinsed. The total time for this cleaning step must not be less than 15 minutes.

Next the endoscope is disinfected: it is immersed in a disinfectant solution and then rinsed once again. Finally, it is dried partially by means of a medical compressed-air gun. The latter step last for approximately 5 minutes. The result obtained is not satisfactory: the step is tedious, and in the end residual moisture is still present at least in part of the channels, which does not guarantee optimum innocuousness.

For more effective drying of an endoscope there exist storage cabinets for heat-sensitive endoscopes (SCHE). Depending on the manufacturer and the type of endoscope, the drying is carried out for between 15 and 90 minutes.

In both cases, the method is lengthy, and must be repeated after each use (SCHE). An endoscope that is cleaned and not dried must be used within a maximum period ranging from 6 to 12 hours in France and a maximum of 3 hours in England; if this time is exceeded, the endoscope must be re-cleaned in order to guarantee its innocuousness and to prevent recolonisation thereof by various pathogens. A time as short as this is very constraining since it involves time, numerous manipulations and human resources. The use of an SCHE makes it possible to extend the storage period to 72 hours, by virtue of the drying of the internal channels.

There therefore exists a need to have available a method for drying endoscopes that is effective and quick and does not damage the endoscopes. Furthermore, there exists a need for a drying method that ensures microbiological safety of this type of medical equipment.

Moreover, there exists a need for a method for storing endoscopes that is economical and as automated as possible, and involves a minimum of manipulations and human resources. In addition the method must provide a saving in space and a reduction in the consumption of drying gas and electricity, which are very great for SCHEs.

BRIEF SUMMARY OF THE INVENTION

The present invention responds to all these problems. In particular, the present invention makes it possible to dry endoscopes effectively and quickly. Compared with the prior art, the present invention makes it possible in particular to gain at least an order of magnitude (a factor of 10) for drying endoscopes. It is furthermore used under conditions compatible with the sensitivity of the apparatus. Finally, it makes it possible to effectively store the cleaned and dried endoscopes for a period much greater than 12 hours, preferably greater than 72 hours, and this in an easy and rapid fashion.

DETAILED DESCRIPTION OF THE INVENTION

Figure 1:
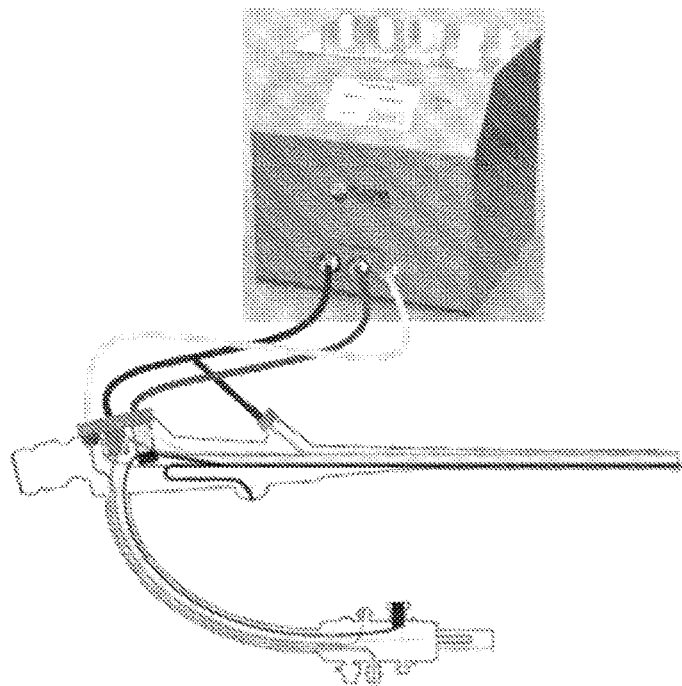
FIG. 1 shows the connection of the endoscope to a drying unit through the piston cage of the endoscope.

The present invention therefore relates to a method for drying channels of an endoscope, comprising the following steps:

a) connecting an endoscope, in particular via a specific connection, to a drying unit, b) injecting a neutral gas into the endoscope channels for a period of between 10 and 60 seconds, the flow rate of the gas being low, the gas being injected at a temperature of between 10° C. and 30° C., in particular to eliminate the residual water, c) drying the channels of the endoscope for a period of between 30 and 150 seconds, by injecting a gas at a high rate, the gas being injected at a temperature of between 30° C. and 60° C. The gas used in step c) may be neutral or a plasma generated by an electrical discharge in a flow of dinitrogen or air, preferably medical air.

Preferably, the total duration of steps a) to c) is between 1 and 5 minutes. This therefore affords ultra-rapid drying and, when the gas is a plasma, complementary disinfection. The complementary disinfection is not obligatory but may overcome any risk of contamination with the rinsing water, after conventional disinfection.

"Cleaning" means that the endoscope has undergone a washing operation. This operation may in particular be done manually or in a washing machine. Any soiling is then removed from the endoscope and it is ready to undergo a disinfection cycle. Preferably, in the method according to the invention, the endoscope is previously cleaned.

"Disinfection" or "disinfecting" an element means the operation of intentional and brief elimination of certain germs, so as to stop or prevent infection or risk of infection or secondary infection by pathogenic and/or undesirable microorganisms (bacteria, protozoa or viruses). Disinfection is distinct from sterilisation, which consists of the definitive elimination of certain germs.

Disinfection involves killing or inactivating pathogen microorganisms from contaminated elements, by altering their structure or inhabiting their metabolism or some of their vital functions.

Disinfection is therefore a particular decontamination mode, i.e. targeted on pathogenic microorganisms (bacteria, protozoa and viruses). Preferably, in the method according to the invention, the endoscope is chemically disinfected prior to steps a) to c).

Chemical disinfection means disinfection by means of chemical products such as enzymatic detergents (amylases, lipases, proteases, etc.), amine compounds, glucoprotamine, peracetic acid and hydrogen peroxide.

The endoscope according to the invention is any type of endoscope. It is composed of a tube comprising channels (which will be introduced into the body of the patient), to which there are connected a control handle and a light guide that allows the fixing of a camera and light.

The endoscope may in particular be chosen from:
bronchoscopes,
digestive endoscopes, such as colonoscopes, gastroscopes, duodenoscopes and echoendoscopes.
paediatric bronchoscopes (which have channels with a smaller diameter than conventional bronchoscopes), urethroscopes and cystoscopes.

Preferably, the duration of step c) is between 120 and 150 seconds for digestive endoscopes, such as colonoscopes, gastroscopes, duodenoscopes and echoendoscopes. Preferably, the duration of step c) is between 1 and 2 minutes for bronchoscopes. Finally, preferably, the duration of step c) is between 1 minute and 90 seconds for paediatric bronchoscopes, cystoscopes and urethroscopes.

The first step of the method according to the invention, i.e. step a), comprises the connection of the endoscope to a drying unit in order to inject the gas.

Figure 2:
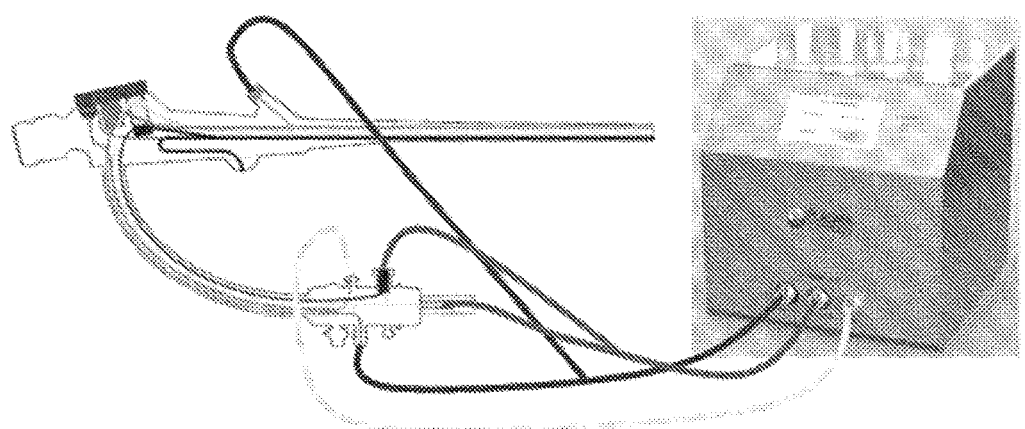
FIG. 2 shows the connection of the endoscope to a drying unit through the distal end of the endoscope.

This connection can be done either through the piston cage of the endoscope, or through its proximal end. In addition, this connection can be done by a dedicated connection, for example by the one sold by Lancer Getinge. An example of this connection through the piston cage is presented in FIG. 1, and an example of this connection by the proximal end is presented in FIG. 2. Preferably, the dedicated connection is fluidtight.

Then, after step a), steps b) and c) arrive: while step b) relates to the injection of a neutral gas at low rate and at a temperature of between 10° C. and 30° C., step c) relates to the injection of a gas at high rate and at a temperature of between 30° C. and 60° C.

More precisely, the conditions used in step b) allow a laminar flow of the residual liquid, in particular of the residual water and of the drying gas, present in the channels. This laminar flow is characterised by a Reynolds number below 2300. This avoids the fragmentation of the residual water and the creation of liquid droplets on the walls of the channels.

On the other hand, the conditions used in step c) allow a turbulent flow of the drying gas. This turbulent flow is characterised by a Reynolds much higher than 2300. This makes it possible to expel and/or evaporate the remaining liquid fraction, and thus ensures rapid and effective drying.

Precisely, during step b), a neutral gas is injected into the endoscope channels for a period of between 10 and 60 seconds, the flow rate of the gas being low, the gas being injected at a temperature of between 10° C. and 30° C., in particular in order to eliminate the residual water. Low rate means a rate of between 1 and 20 liters/minute.

Preferably, the neutral gas is dinitrogen, or air, preferably medical air.

This step b) is short, i.e. a few tens of seconds; it allows the effective discharge of the liquid contained in the channels of the endoscope.

This step b) makes it possible in particular to eliminate the residual water, in particular the water resulting from the previous step of chemical disinfection of the endoscope.

Finally, the method according to the invention comprises a drying step c) for a period of between 30 and 150 seconds, preferably between 60 and 140 seconds, by the injection of gas at high rate and at a temperature between 30° C. and 60° C. High rate means a rate of between 20 and 100 liters/minute. Preferably, the gas used in this step c) is a neutral gas, preferentially dinitrogen or air. Alternatively, the gas is a plasma generated by an electrical discharge in a flow of dinitrogen or air.

The drying is therefore done by the injection of gas, and the disinfection is done simultaneously with the drying when the gas is a plasma.

Preferably, the drying c) is done by the injection of gas into the channels of endoscope either through the piston cage or through its proximal end.

Preferably, the plasma is obtained by the activation, by an electrical field, at atmospheric pressure, of the flow of dinitrogen. Preferably, the plasma is used at a temperature of between 20° C. and 80° C., preferably at a temperature of between 30° C. and 50° C.

Plasmas can be considered to be the fourth state of matter, following, in increasing order of energy, the solid, liquid and gaseous states. This fourth state is strictly speaking a low-density medium, neutral overall, composed of atoms, molecules, ions and free electrons.

Man-made plasmas usually come from a gas or a mixture of gases (Ar, He, air, $O_2$, $N_2$, etc) subjected to an electrical field (between two electrodes). The zone where the gas is subjected to the electrical field is referred to as the "electrical discharge" zone, the plasma flow emanating from this discharge being situated in the "post-discharge" zone.

Conventionally, the plasma is generated by an electrical discharge (by means of an electrical field established between two electrodes) in a flow of gas or of a gaseous mixture that is initially inert. Two plasma zones can be distinguished, the discharge zone and the post-discharge zone. In the discharge zone, electrons, ions, atoms and molecules can be found in various energy states. In the post-discharge zone, the active species found are rather neutral atoms and molecules, which are in excited or metastable states.

Preferably, the plasma used according to the invention is a cold plasma obtained in a post-discharge zone. Preferably, it is precisely obtained by subjecting the flow of dinitrogen to a pulsed electrical field established between two or four electrodes in the form of spikes. The electrical field is created by a high-voltage (kV) pulse generator.

Preferably, the flow of dinitrogen is created upstream of its introduction into the generator by the generation of a flow of dinitrogen at a rate of approximately 1 to 100 liters/minute, preferably at a pressure of 1-2 bar. The flow rate of the gaseous flows is regulated by means of apparatus available commercially, such as the Bronkhorst MASS-VIEW flow regulator.

Preferably, the plasma used according to the invention is generated as follows: the dinitrogen introduced into the generator passes through a discharge chamber (reactor) consisting of a strong thermally insulating material stable at very high temperatures (i.e. above 900° C., preferably around 1000° C.). Preferably, the thermally insulating material stable at very high temperatures is a mixture of ceramic and glass, for example the MACOR® material (55% fluorophlogopite mica and 45% borosilicate glass) marketed by Corning Inc. A channel with a variable diameter, i.e. of around a few mm, pierced inside a cube made from strong thermally insulating material stable at very high temperatures, preferably made from MACOR®, serves for the passage of gas. One or two channels with a diameter of 1 mm are pierced perpendicularly with respect to the gas flow channel. The electrodes, made from pure tungsten and in the form of spikes, are inserted in these channels and sealed. The distance between the spikes of the electrodes is a few mm.

Once the flow of dinitrogen is established in the reactor, it is possible to start the high-voltage nanosecond pulse generator. The high voltage (1-10 kV) created by the generator is used to establish an electrical field between the electrodes in the reactor, with a frequency of between 10 and 100 kHz, preferably between 30 and 80 kHz. The voltage between the electrodes increases and, once the initiation voltage between the electrodes is reached, the discharge occurs in the reactor. On initiation, the voltage between the electrodes drops very quickly and the discharge current achieves the form of a peak with a width halfway up of around 10 ns. The plasma created during this discharge has a temperature of around 300-340 K (i.e. 26.85-66.85° C.) and propagates over a few meters in the endoscope tubes.

Preferably, the apparatus used for generating the plasma is the InPulse ONE generator, marketed by PlasmaBiotics SAS.

Preferably, the plasma according to the invention is obtained and used at atmospheric pressure.

More preferentially, the plasma is obtained, in the plasma drying unit, by the following steps:
passage of a flow of a flow of dinitrogen, having a flow rate of approximately 1 to 100 liters/minute, in the unit; then
subjection of the flow obtained to an electrical discharge.

The method according to the invention comprises the putting of the channels of the endoscope in contact with the plasma.

Preferably, the putting in contact takes place when the plasma has a temperature of between 20° C. and 80° C., preferably a temperature between 30° C. and 50° C.

Preferably, the putting of the element in contact with the plasma takes place during a very short period, i.e. approximately 5 to 60 seconds.

The method for drying channels of an endoscope according to the invention preferably comprises the following steps:
a) connecting the channels of the endoscope, in particular by a fluidtight dedicated connection, to a drying unit,
b) injecting a neutral gas, preferably air, into the endoscope channels for a period of between 10 and 60 seconds, the flow rate of the gas being between 1 and 20 liters/minute, the gas being injected at a temperature between 10° C. and 30° C., in particular in order to eliminate the residual water by a laminar flow, then
c) drying the channels of the endoscope for a period of between 30 and 150 seconds, by injecting the same neutral gas as at b), at a flow rate of between 20 and 100 liters/minute, the gas being injected at a temperature of between 30° C. and 60° C., in particular in order to ensure a turbulent flow of the residual water.

In addition, the method according to the invention may comprise, after step c), the following steps:
d) disconnecting the endoscope obtained at step c) from the drying unit and placing it in an airtight receptacle;
e) injecting a plasma generated by an electrical discharge in a flow of dinitrogen or air into the airtight receptacle, and then closure of said receptacle.

The airtight receptacle is typically a plastic bag, the closure of which is airtight, and comprising an opening for injecting a gas. Such a bag is marketed by PlasmaBiotics under the reference PlasmaBAG.

The endoscope is thus disconnected from the drying unit at step d) and placed in such a receptacle.

Next, a plasma is injected into such a receptacle, for example for a period of a few seconds, preferably a period of between 3 and 10 seconds. This is step e). This step makes it possible to disinfect the air contained inside the receptacle containing the endoscope. Once closed, the endoscope contained in the receptacle can be stored for a period of at least 24 hours, preferably at least 48 hours, preferably at least 72 hours.

This method, comprising steps d) and e), is a method for drying and storing an endoscope. It allows the storage of the endoscope under optimum conditions, in particular for several days (i.e. at least 2 days, preferably at least 3 days), which ensures optimum innocuousness. This is in particular demonstrated in the examples.

The invention will now be exemplified by means of the following examples, which are not limitative.

Example 1

The following tests are carried out in order to compare the drying method according to the invention with the conventional methods with storage cabinets for heat-sensitive endoscopes (SCHE).

Two endoscopes are used for carrying out these tests:
a Fujinon EC530; and
an Olympus CF20HL.

The drying times are indicated in the following table:

| Type of endoscope | Drying time by the method according to the invention | Drying time in SCHE (comparative) |
| --- | --- | --- |
| FUJINON EC530 | 2 minutes and 15 seconds | 90 minutes |
| Olympus CF20HL | 2 minutes and 15 seconds | 60 minutes |

The method according to the invention therefore provides a drying approximately 25 to 40 times more rapid.

The biocidal effect of the nitrogen plasma, incorporated in the method according to the invention is shown on tubes 3 meters long:

| Germs | 4 mm diameter tube | 2.5 mm diameter tube | 1.5 mm diameter tube |
| --- | --- | --- | --- |
| *P. aeruginosa*, $N_2$ plasma drying | 5 log | 4.6 log | 4.2 log |
| *P. aeruginosa*, $N_2$ drying | 3.5 | 3.5 | 3.5 |

Example 2: Evaluation of the Efficacy of the Method for Drying Internal Channels of Several Endoscopes According to the Invention The objective of the study is to evaluate the drying capacity of the internal channels of several endoscopes by the method according to the invention.

This study uses clause 6.2.3 of NF S098-030, relating to the drying of endoscopes in SCHE.

Although the drying method according to the invention cannot be considered to be a cabinet, the objectives of this method can be likened to those of an SCHE.

1) Equipment and Methods

At the end of the cleaning/disinfection cycle, the channels of the endoscopes are purged and a wiping of the orifices (aspiration, air/water and biopsy orifices) is carried out. The channels are next connected to the Typhoon drying unit (PlasmaBiotics) (step a)) and then subjected to the drying method according to the invention (steps b) and c)): insufflation of nitrogen and then treatment with nitrogen plasma).

In accordance with NF S098-030, once the drying cycle is performed, compressed air of medical quality at a pressure of 105 to 120 kPa is blown into each channel of the endoscope in turn, with the distal end of the endoscope positioned between 50 mm and 100 mm above and perpendicular to a coloured crepe paper.

The efficacy of the drying phase is considered to be satisfactory if no droplet of moisture is visible on the crepe paper.

The specific operating conditions of the drying are as follows:

| Nature of cycle according to type of endoscope | Duration of drying | Maximum T° at the inlet of the endoscope |
| --- | --- | --- |
| Gastroscope | 135 seconds | 45° C. |
| Colonoscope | | |
| Duodenoscope | | |
| Echoendoscope | | |
| Bronchoscope | 90 seconds | 45° C. |
| Paediatric bronchoscope | 60 seconds | 40° C. |

The endoscopes tested are as follows:
a) Olympus:
  Colonoscopes: CF Q160 I, CF Q180 AI
  Gastroscopes: GIF Q160, GIF Q180.
b) Fujinon:
  Colonoscopes: EC250WM. EC450WM5-H and EC250WM5,
  Gastroscopes: EG410HRS, EG250WR5,
  Duodenoscope: ED410XT.
c) Pentax:
  Colonoscopes: EC3880FK, EC380MK,
  Gastroscope: EG2940K,
  Bronchoscope: FB15V
2) Results:

All the results of the drying tests carried out the colonoscopes, gastroscopes, duodenoscope and bronchoscope show no trace of moisture.

With regard to these results, it is concluded that the drying method according to the invention has an efficacy of drying equivalent to the SCHEs in NF S098-030.

Example 3: Evaluation of the Drying Method According to the Invention on the Microbiological Quality of the Endoscope Channels The objective of the study is to evaluate the effect of the method according to the invention on the microbiological quality of endoscope channels, in comparison with a standard drying method (manual drying with air).

This study used clause 4.2.4 of NF S098-030 relating to the drying of endoscopes in SCHE.

Although the drying method according to the invention cannot be considered to be a cabinet, the objectives of this method can be likened to those of an SCHE.

1) Equipment and Methods

The method used is identical to the one at point 1 of example 2.

The specific operating conditions of the drying are as follows:

| Nature of cycle according to type of endoscope | Duration of treatment | Maximum T° at inlet of endoscope |
| --- | --- | --- |
| Colonoscope | 135 seconds | 45° C. |

The endoscope tested is the Pentax colonoscope EC3880FK.

Microbial Strains:
*P. aeriginosa* CIP103467
Diluent of the microbial suspensions: tryptone salt (OXOID, TV5016D).
Sampling Solution:

| | |
| --- | --- |
| Lecithin (SIGMA, P-5394) | 0.3% (w/v) |
| Sodium thiosulfate (SIGMA, S-8503) | 0.5% (w/v) |
| Polysorbate 80 (SIGMA, p-1754) | 3.0% (w/v) |
| L-Histidine (SIGMA, H-8000) | 0.1% (w/v) |
| Distilled water | qsp 100 ml |
| N° of internal batches | D100.1.1, D 130.1.2, D130.1.5, D149.1.2 |

Sterilised in moist heat at 121° C. for 20 minutes.
Maintenance and accounting medium: tryptone soya (OXOID, CM0131).

The sampling is carried out by injection of 50 ml of sampling solution via the cleaning adapter (sampling of the air/water channels), 50 ml via the aspiration coupling (sampling of the aspiration/biopsy channel), 20 ml via the inlet of the water-jet channel and 50 ml via the orifice of the operator channel The four volumes are recovered at the distal end and were analysed by dilution/inclusion and filtration on 0.45 μm membrane. The membranes are deposited on gelose and incubated for 48 hours at 37° C. After incubation, the colonies are counted and the results expressed as a number of viable microorganisms per endoscope.

The endoscope is contaminated by injecting 15 ml of the test microbial suspension (strain in its diluent) containing between $1.5 \times 10^4$ UFC/ml and $5 \times 10^4$ UFC/ml at the rate of 6 ml via the aspiration coupling, 6 ml via the air nozzle and 3 ml for the water-jet channel. After 30 minutes of incubation, the channels are purged with 50 ml of air and then maintained at ambient temperature for 30 minutes.

Figure 3:
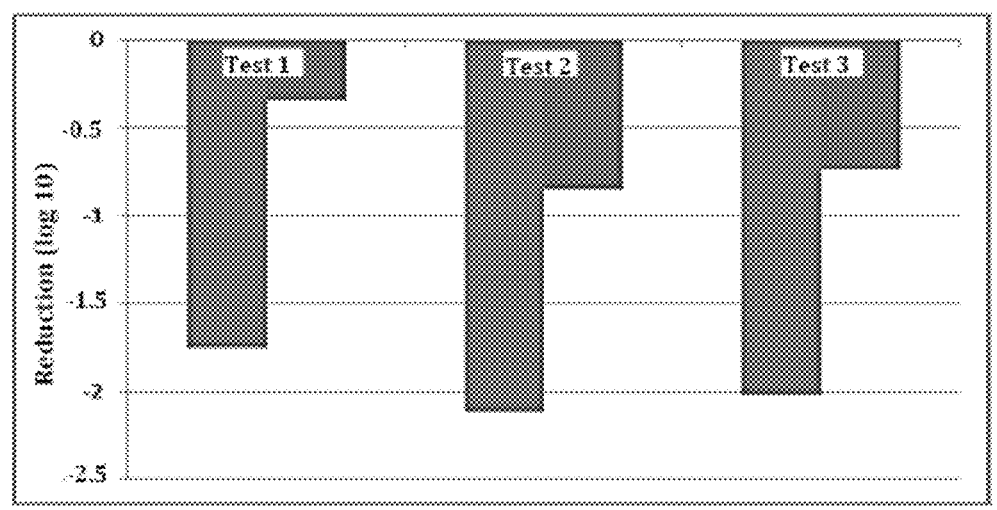
FIG. 3 shows the change in the internal microbial contamination of the colonoscopes subjected to drying according to the invention (second series of columns), compared with the contamination level subjected to the standard method (blowing with medical air, first series of columns).

2) Results:
The results are presented in FIG. 3:
FIG. 3 shows the change in the internal microbial contamination of the colonoscopes subjected to drying according to the invention (second series of columns), compared with the contamination level subjected to the standard method (blowing with medical air, first series of columns).

The results show that the level of contamination of the internal channels of the endoscope dried according to the invention:
  remains less than the initial contamination level of the endoscope before drying; and
  is always less than that of the endoscope subjected to the standard method.

Example 4: Evaluation of the Efficacy of the Drying Method According to the Invention Including Storage The objective is to evaluate the abilities of the drying and storage method according to the invention (steps a) to e)) to maintain the microbiological quality of the endoscopes, according to a methodology inspired by NF EN 16442:2015 (SCHE standard)

Equipment:
FUJINON EC 250 WM endoscopes
Plasma Typhoon (PlasmaBiotics)
Connection kit for connecting the endoscopes to the Plasma Typhoon
PlasmaBAG (endoscope storage bags)

1. Step 1: Preparation of the Endoscopes

The procedure for preparing the endoscope is identical for all the endoscopes analysed.

1. Subjecting the endoscope to a standard cleaning/disinfection cycle
2. Contaminating the endoscope artificially by injecting into each of the channels a contamination solution containing approximately $1.5 \times 10^3$ to $5 \times 10^3$ *Pseudomonas aeruginosa*/ml
3. Maintaining the endoscope at ambient temperature for 30 minutes.
4. Purging the endoscope channels in order to eliminate any excess contamination solution
5. Maintaining the endoscope at ambient temperature (for 1 hour or according to the instructions of the manufacturer)

After the incubation period, the endoscope is subjected to the drying and storage method according to the invention. In total:

3 tests are carried out by sampling the endoscope just after the purge in order to determine the level of contamination of the endoscope before drying and storage (control);

2 tests are carried out by sampling the endoscope after 24 hours, 48 hours and 72 hours of storage according to the method to be tested (test according to the invention); and 2 tests are carried out by sampling the endoscope after 24 hours, 48 hours and 72 hours of storage outside (standard storage method).

Drying and Storage Method According to the Invention

2. Step 2: Drying of the Endoscopes (Steps a) to c))

The drying method is carried out using Plasma Typhoon:
At the start of the tests:
1. Open the gas bottle, adjust the pressure to 3 bar. In the case of the use of medical air, adjust the pressure to 3 bar.
2. Power up Plasma Typhoon (ON)

For each drying cycle:
3. Connect all the endoscope channels to the plasma outlets of the Plasma Typhoon using the connection kit:
   a. Suction/Operating channel
   b. Air/Water channel
   c. Water jet channel
4. Put the bridge at the proximal end of the endoscope (in the case of gastroscope, colonoscope, duodenoscope, echoendoscope)
5. Start the drying cycle
6. Once the cycle is completed, disconnect the endoscope.

3. Step 3: Storage of Endoscopes (Steps d) and e))

Once dried, the endoscopes are stored in polyethylene bags:
1. Place the endoscope in the polyethylene bag (PlasmaBAG)
2. Close the bag using the zip on the side
3. Connect the Plasma Typhoon to the luer placed in the corner of the bag
4. Choose the "storage" cycle
5. Start the "storage" cycle, which serves to blow plasma into the bag for 5 seconds
6. Once the cycle is completed, disconnect the Plasma Typhoon from the bag (luer) and close the bag with a luer stopper.

Analysis:

The efficacy of the storage methods is determined by comparing for each of the contact times the level of contamination of the endoscope stored according to the method with an endoscope not blown with the Typhoon and kept outside.

The results are as follows:

| Test | Storage time | Count (UFC/ml) |
| --- | --- | --- |
| According to the invention | 24 hours | 1 |
| Standard | 24 hours | $24 \times 10^7$ |
| According to the invention | 48 hours | 0 |
| Standard | 48 hours | $1.9 \times 10^9$ |
| According to the invention | 72 hours | 0 |
| Standard | 72 hours | $3.1 \times 10^9$ |

The drying and storage method according to the invention thus makes it possible to maintain the microbiological quality of the endoscope for a period of at least 72 hours.

The invention claimed is:

1. A method for drying at least one channel of a device, comprising the following steps:
   a) injecting a non-reactive gas into the at least one channel of the device to eliminate residual water by a laminar flow regime,
   b) drying the at least one channel of the device, by injecting a second gas having a turbulent flow regime, the second gas being injected at a temperature of between 30° C. and 60° C.

2. The method according to claim 1, wherein it comprises, after step b), the following steps:
   c) placing the device in a receptacle that is airtight when closed;
   d) injecting a plasma generated by an electrical discharge in a flow of dinitrogen or air into the airtight receptacle, and then closure of said receptacle.

3. The method according to claim 1, wherein the non-reactive gas is dinitrogen or air.

4. The method according to claim 1, wherein the gas used in step b) is non-reactive, or is a plasma generated by an electrical discharge in a flow of dinitrogen or air.

5. The method according to claim 1, wherein the non-reactive gas injected in step a) is injected into the at least one channel of the device for a period of between 10 and 60 seconds.

6. The method according to claim 1, wherein the non-reactive gas injected in step a) is injected into the at least one channel of the device at a temperature of between 10° C. and 30° C.

7. The method according to claim 1, wherein the second gas injected in step b) is injected into the at least one channel of the device for a period of between 30 and 150 seconds.

8. The method according to claim 2, wherein the plasma injected in step d) is injected into said receptacle for a period of between 3 and 10 seconds.

9. The method according to claim 1, wherein the device is an endoscope.

10. The method according to claim 9, wherein the drying of step b) is done by injecting the second gas into the at least one channel of the endoscope through a piston cage, or through its proximal end.

11. The method according to claim 1, wherein the total duration of steps a) to b) is between 1 and 5 minutes.

12. The method according to claim 9, wherein the endoscope is chemically disinfected prior to step a).

13. The method according to claim 2, wherein, after step d), said receptacle can be stored for a period of at least 24 hours.

14. The method according to claim 2, wherein, after step d), said receptacle can be stored for a period of at least 72 hours.

15. The method according to claim 1, wherein the step a) is preceded by a step of connecting said device to a drying unit.

16. The method according to claim 2, wherein the step a) is preceded by a step of connecting said device to a drying unit and said method comprising between steps b) and c), a step of disconnecting said device.

* * * * *